US012667563B2

(12) United States Patent (10) Patent No.: US 12,667,563 B2
Suzuki et al. (45) Date of Patent: Jun. 30, 2026

(54) PROPHYLACTIC OR THERAPEUTIC AGENT FOR PORPHYRIA

(71) Applicant: TANABE PHARMA CORPORATION, Osaka (JP)

(72) Inventors: Tsuyoshi Suzuki, Osaka (JP); Masahiro Kondo, Osaka (JP); Fumihiro Takahashi, Osaka (JP); Akihito Ogasawara, Osaka (JP); Kazumi Hyoudou, Osaka (JP)

(73) Assignee: TANABE PHARMA CORPORATION, Osaka (JP)

( * ) Notice: Subject to any disclaimer, the term of this patent is extended or adjusted under 35 U.S.C. 154(b) by 573 days.

(21) Appl. No.: 18/009,107

(22) PCT Filed: Jun. 10, 2021

(86) PCT No.: PCT/JP2021/022036
§ 371 (c)(1),
(2) Date: Dec. 8, 2022

(87) PCT Pub. No.: WO2021/251450
PCT Pub. Date: Dec. 16, 2021

(65) Prior Publication Data
US 2023/0248713 A1 Aug. 10, 2023

(30) Foreign Application Priority Data

Jun. 10, 2020 (JP) ................................. 2020-100952
Aug. 7, 2020 (JP) ................................. 2020-134451

(51) Int. Cl.
*A61K 31/454* (2006.01)
*A61P 7/00* (2006.01)
(52) U.S. Cl.
CPC .............. *A61K 31/454* (2013.01); *A61P 7/00* (2018.01)
(58) Field of Classification Search
CPC .............. A61K 31/454; A61K 31/4545; C07D 401/14; A61P 7/00; A61P 17/00
See application file for complete search history.

(56) References Cited

U.S. PATENT DOCUMENTS

2015/0152107 A1 6/2015 Herrera Ruiz et al.
2017/0190697 A1 7/2017 Yamamoto et al.
2022/0073497 A1 3/2022 Ueda et al.

FOREIGN PATENT DOCUMENTS

RU        2 634 713            11/2017
WO        2008/025094          3/2008
WO        WO 2015/182723    *  12/2015
WO        2020/138481          7/2020

OTHER PUBLICATIONS

Office Action with Search Report issued Jul. 25, 2023 in corresponding Russian Patent Application No. 2023100029, with English translation.
Kharkevich, D.A., Pharmacology: Textbook, 9th ed., revised, supplemented and corrected. M: Geotar Media, (2006), pp. 2-4, 39, 63, 569.
International Search Report issued Jul. 20, 2021, in International (PCT) Application No. PCT/JP2021/022036, 2 pages.
Minder et al., "Pharmacokinetics and Pharmacodynamics of Afamelanotide and its Clinical Use in Treating Dermatologic Disorders", Clinical Pharmacokinetics, 2017, vol. 56, pp. 815-823, 9 pages.
Extended European Search Report issued Jun. 7, 2024 in corresponding European Patent Application No. 21821230.6.
Manisha Balwani et al., "Erythropoietic Protoporphyria: Phase 2 Clinical Trial Results Evaluating the Safety and Effectiveness of Dersimelagon (MT-7117), an Oral MC1R Agonist", Blood, vol. 136, Issue Supplement 1 (2020), pp. 1-6.
Office Action issued Apr. 24, 2025 in corresponding Korean Patent Application No. 10-2022-7045682, with English translation.
Schultheiss et al., "Pharmaceutical Cocrystals and Their Physicochemical Properties", Crystal Growth & Design, 2009, vol. 9, No. 6, pp. 2950-2967.

* cited by examiner

*Primary Examiner* — Sahar Javanmard
(74) *Attorney, Agent, or Firm* — Finnegan, Henderson, Farabow, Garrett & Dunner, LLP

(57) ABSTRACT

A medicament for treatment or prevention of porphyria, comprising 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof as an active ingredient, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof is 50 to 500 mg/day.

20 Claims, No Drawings

PROPHYLACTIC OR THERAPEUTIC AGENT FOR PORPHYRIA

BACKGROUND OF THE INVENTION

Field of the Invention

The present invention relates to a pharmaceutical composition for treatment or prevention of porphyria, comprising a compound having melanocortin receptor (MCR) agonistic activity (agonist activity).

Description of the Related Art

Among the light radiated from the sun, the rays having wavelengths allot more than 300 nm are absorbed in the ozone layer in the stratosphere. Thus, the sunlight that reaches the ground is composed of ultraviolet light having wavelengths of not less than 300 nm, visible light, and infrared light. Physiological reactions caused by exposure to the sunlight include solar dermatitis (sunburn), and skin changes (wrinkling, sagging, and development of pigmented spots) called photoaging that occur due to long-term exposure. On the other hand, there are diseases called photodermatoses, in which pathological changes such as dermatitis occur due to light irradiation even when the light irradiation is at a level at which healthy individuals do not respond. One known example of photodermatoses is porphyria.

Porphyria is a disease that develops due to accumulation of porphyrins or precursors thereof as a result of decreased activity of heme metabolic enzyme. Porphyria may exhibit symptoms such as photosensitivity (sunburn, burn-like symptoms), and also gastrointestinal symptoms and neurological symptoms. Once porphyria develops, its symptoms often continue throughout life. Since there is no curative treatment therefor, symptomatic treatment such as light shielding is carried out as the main therapeutic method.

For example, Patent Document 1 discloses use of MCR agonist peptides such as afamelanotide for the purpose of treatment of photodermatoses such as erythropoietic protoporphyria. However, since afamelanotide is not an MC1R-selective agonist, there is a concern of the occurrence of side effects. Moreover, since afamelanotide is a peptide, it cannot be orally administered, and its half-life is short. Thus, there is a problem that periodic subcutaneous implanting by a medical professional is required.

On the other hand, Patent Document 2 discloses that pyrrolidine compounds such as 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid, and pharmaceutically acceptable salts, solvates, hydrates, cocrystals, and the like thereof have excellent MCR-, especially MC1R-, activating action. Patent Document 2 discloses that the compounds are useful for prevention or treatment of diseases or symptoms associated with activation of MCR, especially MC1R, and that such diseases include protoporphyria. However, the document does not specifically describe their doses.

Patent Document 3 discloses a cocrystal of 1-{2-[(3S, 4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid. However, the document does not specifically describe the dose of the coctystal of 1-{2-[3S, 4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid for use in treatment of porphyria.

PRIOR ART DOCUMENTS

Patent Documents

[Patent Document 1] WO 2008025094
[Patent Document 2] WO 2015182723
[Patent Document 3] WO 2020/138481

SUMMARY OF THE INVENTION

Problems to be Solved by the Invention

Methods of curative treatment of porphyria are limited, and the main method for avoiding development of symptoms or for alleviation of symptoms has been prevention of exposure of the skin to sunlight. In particular, it is known that patients with photodermatoses induced by visible light tend to avoid going out in the daytime, so that the quality of life (QOL) of the patients may be remarkably deteriorated.

As described above, an analog of et-melanocyte-stimulating hormone (α-MSH), which is a ligand of MCR, has been developed as a therapeutic agent for photodermatoses and the like such as erythropoietic protoporphyria (Patent Document 1). However, it is not an MC1R-selective agonist, and cannot be orally administered since it is a peptide. Moreover, since it disappears quickly in the human body, periodic implanting is required.

Therefore, a pharmaceutical composition for treatment or prevention of porphyria, which pharmaceutical composition is safer and not burdensome for patients, and which enables effective treatment, is demanded.

Means to Solve the Problems

In order to solve the above problems, the present inventors intensively studied. As a result, the present inventors discovered a dose of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof, which dose is especially effective in a human clinical trial and exerts an excellent therapeutic or prophylactic effect on porphyria including erythropoietic protoporphyria (EPP) and X-linked porphyria. In particular, a dose at which a significant pharmacological effect can be produced relative to placebo not only in seasons with strong sunlight for long time such as spring and summer in the Northern Hemisphere, but also in seasons with weak sunlight for short time such as fall and winter in the Northern Hemisphere, that is, a dose at which effective treatment or prevention of porphyria is possible throughout the year, could be discovered. The preceding agent afamelanotide has been confirmed to have a therapeutic effect on symptoms that occur after exposure to direct sunlight in a clinical trial. In contrast, at the dose in the present invention, 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof was confirmed to exert a therapeutic effect not only on symptoms caused by exposure to direct sunlight, but also on symptoms caused by exposure to indirect sunlight that may occur even in the inside of a building or the like. The present invention was completed based on such findings.

The present invention provides a medicament fir treatment or prevention porphyria such as erythropoietic protoporphyria or X-linked porphyria, the medicament comprising 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or a pharmaceutically acceptable salt or cocrystal thereof as an active ingredient, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof is 50 to 500 mg/day, preferably 100 to 300 mg/day.

The present invention provides a method of treatment or prevention of porphyria such as erythropoietic protoporphyria or X-linked porphyria, the method comprising the step of administering an effective amount of 1-{2-[(3S,4R)-1-{[(3R,4R)-1-cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof to a subject in need of treatment or prevention, wherein the effective amount is 50 to 500 mg/day, preferably 100 to 300 mg/day.

The present invention provides 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof, for treatment or prevention of porphyria such as erythropoietic protoporphyria or X-linked porphyria, wherein the dose of the 1-{2-[(3S,4R)-1-{[(R3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof is 50 to 500 mg/day, preferably 100 to 300 mg/day.

The present invention provides use of 1-{2-[(3S,4R)-1-{[(3R,4R)-1-cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof, in manufacture of a medicament for treatment or prevention of porphyria such as erythropoietic protoporphyria or X-linked porphyria, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof is 50 to 500 mg/day, preferably 100 to 300 mg/day.

According to the present invention, treatment or prevention of porphyria is possible in any environment either indoors or outdoors throughout the year. 1-{2-[(3S,4R)-1-{[(3R,4R)-1-Cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof can be orally administered, and exhibits excellent kinetics in the human body. Moreover, since it is an MC1R-selective compound, it causes less side effects, and enables safe and effective treatment or prevention of porphyria without imposing a burden on the patient. In particular, in porphyria such as erythropoietic protoporphyria or X-linked porphyria, administration of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof at a particular dose enables excellent therapeutic effects such as prolongation of the time to the occurrence of phototoxicity (in other words, time to occurrence of phototoxicity-related symptom or time to prodromal symptoms), reduction of pain events, and improvement of QOL, either indoors or outdoors throughout the year.

DETAILED DESCRIPTION OF THE INVENTION

The present invention is described below
<Active Ingredient>

The active ingredient of the medicament of the present invention, that is, 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof, is described in Patent Document 2, and can be produced by, for example, the method described in Patent Document 2. A cocrystal of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid and phosphoric acid can be obtained by a conventional method or, for example, the method described in Patent Document 3.

In this specification, the "dose of the 1-{2-[(3S,4R)-1-{[(3R,4R)-1-cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof" or the dose or amount of "Compound A" refers to the dose or amount in terms of the amount of {2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid as free form.

<Pharmaceutical Application>

Since 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof has excellent MC1R agonist activity, it exerts excellent therapeutic and prophylactic effects on porphyria, such as prolongation of the time to the occurrence of phototoxicity, reduction of pain events, and improvement of QOL, in any environment throughout the year.

Further, 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically, acceptable salt or cocrystal thereof exerts an especially excellent effect on prolongation of the time to the occurrence of phototoxicity in a particular patient group (patient group whose baseline median of the erythrocyte protoporphyrin IX level is not less than 1980.50 mcg/dL), thereby exerting excellent therapeutic and prophylactic effects on porphyria.

Furthermore, 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof exerts an excellent effect on prolongation of the time to the occurrence of phototoxicity in a particular patient group (patient group whose median of the melanin density is not less than 3.0915) independent of the dose, and exerts an excellent effect on prolongation of the time to the occurrence of phototoxicity in a particular patient group (patient group whose median of the melanin density is less than 3.0915) at a particular dose (preferably at a daily dose of 300 mg), thereby exerting excellent therapeutic and prophylactic effects on porphyria.

Thus, a medicament containing 1-{2-[(3S,4R)-1-{[(3R, 4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof as an active ingredient is useful for treatment or prevention of porphyria.

Examples of the porphyria include erythropoietic protoporphyria, X-linked porphyria, congenital erythropoietic porphyria, variegate porphyria, acute intermittent porphyria, porphyria cutanea tarda, and hereditary coproporphyria.

The erythropoietic protoporphyria herein includes congenital erythropoietic protoporphyria.

The time to the occurrence of phototoxicity has the same meaning of the time to occurrence of phototoxicity-related symptom, or simply a symptom. It also means the time to prodromal symptom. Examples of phototoxicity-related symptom, symptom or prodromal symptom include burning, tingling, itching and stinging.

The 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid may be subjected to the pharmaceutical use either in the free form, or in the form of a pharmaceutically acceptable salt or cocrystal thereof.

Here, the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof includes any of intramolecular salts and adducts, and solvates, hydrates, crystalline polymorphs, and the like thereof.

Examples of the pharmaceutically acceptable salts, cocrystals, intramolecular salts, and adducts include those containing: an inorganic acid such as hydrochloric acid, sulfuric acid, phosphoric acid, or hydrobromic acid: or an organic acid such as acetic acid, fumaric acid, oxalic acid, citric acid, methanesulfonic acid, benzenesulfonic acid, p-toluenesulfonic acid, or maleic acid. Cocrystals with phosphoric acid are especially preferred.

One of, or two or more of, 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid and pharmaceutically acceptable salts and cocrystals thereof may be administered as they are to the patient. Preferably, however, 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof may be mixed with a pharmacologically and pharmaceutically acceptable additive(s) to be provided as a formulation in a form well known to those skilled in the art.

Examples of the pharmacologically and pharmaceutically acceptable additive(s) include appropriate excipients, disintegrants, binders, lubricants, coating agents, colorants, diluents, bases, and isotonic agents usually used in the production of pharmaceuticals. Examples of the excipients include glucose, lactose, D-mannitol, starch, and crystalline cellulose. Examples of the disintegrants include carboxymethyl cellulose, starch, and calcium carboxymethyl cellulose. Examples of the binders include hydroxypropyl cellulose, hydroxypropyl methylcellulose, polyvinyl pyrrolidone, and gelatin. Examples of the lubricants include magnesium stearate and talc. Examples of the coating agents include hydroxypropyl methylcellulose, sucrose, polyethylene glycol, and titanium oxide. Examples of the bases include vaseline, liquid paraffin, polyethylene glycol, gelatin, kaolin, glycerin, purified water, and hard fat. In addition, for formulations suitable for injection or infusion, the following may be used as formulation additives: solvents and solubilizers that may constitute aqueous injection solutions, or may constitute injection solutions to be prepared before use, such as distilled water for injection, physiological saline, and propylene glycol; isotonic agents such as glucose, sodium chloride, D-mannitol, and glycerin; pH regulators such as inorganic acids, organic acids, inorganic bases, and organic bases; and the like.

The 1-[2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl]piperidine-4-carboxylic acid or the pharmaceutically acceptable salt or cocrystal thereof, together with the above-described additives, may be prepared into an appropriate dosage form (such as a powder, an injection solution, a tablet, a capsule, or a topical preparation), and may then be administered to a patient (human or animal) using an appropriate administration method in accordance with the dosage form (such as intravenous administration, oral administration, percutaneous administration, or topical administration). Among these, oral administration is preferred.

The dose of the medicament comprising 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof is an amount at which the medicament can be safely used with low toxicity and at which a therapeutic effect or prophylactic effect can be exerted on porphyria either indoors or outdoors throughout the year. The dose in terms of the amount of 1-{2-[(3S,4R)-1-{[(R3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof is 50 to 500 mg/day, more preferably 80 to 400 mg/day, especially preferably 100 to 300 mg/day. Examples of the dose include 100 mg/day, 150 mg/day, 200 mg/day, 250 mg/day, 300 mg/day, and doses between these.

Oral administration is especially preferred. The dose of the medicament comprising 1-{2-[(3S,4R)-1-{[(R3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof for oral administration, in terms of the amount of 1-{2-[(3S,4R)-1-{[(R3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof is 50 to 500 mg/day, preferably 80 to 400 mg/day, more preferably 100 to 300 mg/day, more specifically, 100 mg/day, 150 mg/day, 200 mg/day, 250 mg/day, 300 mg/day, or a dose between these. The medicament is especially preferably administered at a dose of 100 mg/day, 200 mg/day, or 300 mg/day.

Still more preferably, a cocrystal of 1-{2-[(3S,4R)-1-{[(3R,4R)-1-cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid and phosphoric acid is administered at a dose of 100 mg/day or 300 mg/day in terms of the amount of 1-{2-[R3S,4R)-1-{[(3R,4R)-1-cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid.

Otherwise, preferably, a cocrystal of 1-{2-[(3S,4R)-1-{[(3R,4R)-1-cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid and phosphoric acid is administered at a dose of 100 mg/day or 200 mg/day in terms of the amount of 1-{2-[(3S,4R)-1-{[(R3R,4R)-1-cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid.

In another mode, a cocrystal of 1-{2-[(3S,4R)-1-{[(3R, 4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid and phosphoric acid is administered at a dose of 100 mg/day in terms of the amount of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid.

In another mode, a cocrystal of 1-{2-[(3S,4R)-1-{[(3R, 4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid and phosphoric acid is administered at a dose of 200 mg/day in terms of the amount of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid.

In another mode, a cocrystal of 1-{2-[(3S,4R)-1-{[(3R, 4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid and phosphoric acid is administered at a dose of 300 ma/day in terms of the amount of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid.

As described in the Examples below, it was shown that, at a daily dose of 100 mg or 300 mg, 1-{2-[(3S,4R)-1-{[(3R, 4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof exerts therapeutic effects such as prolongation of the time to the occurrence of phototoxicity, reduction of pain events, and improvement of QOL relative to placebo in patients with erythropoietic protoporphyria and patients with X-linked porphyria. In particular, in a patient group whose baseline median of the erythrocyte protoporphyrin IX level was not less than 1980.50 mcg/dL, a statistically significant effect on prolongation of the time to the occurrence of phototoxicity relative to placebo was found at a daily dose of either 100 mg or 300 mg. According to comparison between a patient group whose median of the melanin density was not less than 3.0915 and a patient group whose median of the melanin density was less than 3.0915, the former group showed similar levels of prolongation of the time to the occurrence of phototoxicity at daily doses of both 100 mg and 300 mg, but, in the latter group, the patient group with a daily dose of 300 mg showed better prolongation of the time to the occurrence of phototoxicity.

Also at daily doses of 100 mg and 200 mg, a test which confirms a therapeutic effect of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof on patients with erythropoietic protoporphyria and patients with X-linked porphyria is conducted.

Although Patent Document 2 and Patent Document 3 describe erythropoietic protoporphyria as a target disease, these documents do not specifically describe doses. In the clinical trial shown in the present invention, it was found that administration at a dose including 100 mg/day and 300 mg/day, for example, 50 to 500 mg/day, preferably 80 to 400 mg/day, more preferably 100 to 300 mg/day, enables exertion of excellent therapeutic effects on erythropoietic protoporphyria either indoors or outdoors throughout the year, which therapeutic effects include prolongation of the time to the occurrence of phototoxicity, reduction of pain events, and improvement of QOL. These finding were not described or suggested in the above documents at all.

Thus, one mode of the present invention provides a medicament to be administered to a patient with porphyria for treatment or prevention of porphyria, the medicament comprising 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof as an active ingredient, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof for the patient with porphyria is 50 to 500 mg/day, preferably 80 to 400 mg/day, more preferably 100 to 300 mg/day, more specifically, 100 mg/day, 150 mg/day, 200 mg/day, 250 mg/day, 300 mg/day, or a dose between these.

In another mode of the present invention, a medicament is administered to a patient with erythropoietic protoporphyria or a patient with X-linked porphyria for treatment or prevention of erythropoietic protoporphyria or X-linked porphyria, wherein the medicament comprises 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof as an active ingredient, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof for the patient with erythropoietic protoporphyria or the patient with X-linked porphyria is 50 to 500 mg/day, preferably 80 to 400 mg/day, more preferably 100 to 300 mg/day, more specifically, 100 mg/day, 150 mg/day, 200 mg/day, 250 mg/day, 300 mg/day, or a dose between these.

In another mode of the present invention, a medicament is administered to a patient with erythropoietic, protoporphyria or a patient with X-linked porphyria for prolongation of the time to the occurrence of phototoxicity and/or reduction of pain events, wherein the medicament comprises 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof as an active ingredient, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof for the patient with erythropoietic protoporphyria or the patient with X-linked porphyria is 50 to 500 mg/day, preferably 80 to 400 mg/day, more preferably 100 to 300 mg/day, more specifically, 100 mg/day, 150 mg/day, 200 mg/day, 250 mg/day, 300 mg/day, or a dose between these.

In another mode of the present invention, a medicament is administered to a patient with erythropoietic protoporphyria or a patient with X-linked porphyria for treatment or prevention of erythropoietic protoporphyria or X-linked porphyria, wherein a patient group is the group whose baseline median of the erythrocyte protoporphyrin IX level is not less than 1980.50 mcg/dL, wherein the medicament comprises 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof as an active ingredient, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof for the patient with erythropoietic protoporphyria or the patient with X-linked porphyria is 50 to 500 mg/day, preferably 80 to 400 mug/day, more preferably 100 to 300 mg/day, more specifically, 100 mg/day, 150 mg/day, 200 mg/day, 250 mg/day, 300 mg/day, or a dose between these.

In another mode of the present invention, a medicament is administered to a patient with erythropoietic protoporphyria or a patient with X-linked porphyria for treatment or prevention of erythropoietic protoporphyria or X-linked porphyria, wherein a patient group is the group whose median of the melanin density is not less than 3.0915, wherein the medicament comprises 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or a pharmaceutically acceptable salt or cocrystal thereof as an active ingredient, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof for the patient with erythropoietic protoporphyria or the patient with X-linked porphyria is 50 to 500 mg/day, preferably 80 to 400 mg/day, more preferably 100 to 300 mg/day, more specifically, 100 mg/day, 150 mg/day, 200 mg/day, 250 mg/day, 300 mg/day, or a dose between these.

In another mode of the present invention, a medicament is administered to a patient with erythropoietic protoporphyria or a patient with X-linked porphyria for treatment or prevention of erythropoietic protoporphyria or X-linked porphyria, wherein a patient group is the group whose median of the melanin density is less than 3.0915, wherein the medicament comprises 1-{2-[(3S,4R)-1-{[(3R,4R)-1-cyclopentyl-3-fluoro-4-(4-methoxyphenyl)pyrrolidin-3-yl]

carbonyl}-4-(methoxymethyl)pyrrolidin-3-yl]-5-(trifluoromethyl)phenyl}piperidine-4-carboxylic acid or a pharmaceutically acceptable salt or cocrystal thereof as an active ingredient, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof for the patient with erythropoietic protoporphyria or the patient with X-linked porphyria is 50 to 500 mg/day, preferably 80 to 400 mg/day, more preferably 100 to 300 mg/day, more preferably 200 to 300 mg/day, more specifically, 100 mg/day, 150 mg/day, 200 mg/day, 250 mg/day, 300 mg/day, or a dose between these, more preferably 150 mg/day, 200 mg/day, 250 mg/day, 300 mg/day, or a dose between these.

EXAMPLES

The present invention is described below more specifically by showing Examples. However, the scope of the present invention is not limited to the embodiments in the following Examples.

Compound A, which was used in the Examples, is the following compound: cocrystal containing 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid and phosphoric acid.

The 1-{2-[(3S,4R)-1-{[(3R,4R)-1-cyclopentyl-3-fluoro-4-(4-methoxyphenyl)pyrrolidin-3-yl]-carbonyl}-4-(methoxymethyl)pyrrolidin-3-yl]-5-(trifluoromethyl)phenyl}piperidine-4-carboxylic acid was produced by the method described in Patent Document 2, and the cocrystal with phosphoric acid was produced by the following method.

More specifically, a solution of potassium carbonate (3.4 kg) in water (77.0 L), and water (19.3 L), were sequentially added to a suspension of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic ½ ethane-1,2-disulfonic acid (19.3 kg) in ethyl acetate (86.6 kg) at 20 to 30° C. and the resulting mixture was stirred for 10 minutes. After leaving the mixture to stand, the aqueous layer was removed, and the organic layer was washed twice with water (96.3 L). After concentrating the organic layer to 35 L, ethanol (75.9 kg) was added thereto, followed by concentrating the resulting mixture to 35 L. The resulting concentrate was diluted with ethanol (30.3 kg), and the insoluble matter was filtered off and washed with ethanol (75.6 kg). The filtrate and washings were combined, concentrated to 35 L, and then diluted with ethanol (17.9 kg). After sequential addition of 24% aqueous sodium hydroxide solution (6.1 kg) and water (15.6 kg) thereto at 20 to 30° C., the resulting mixture was stirred at 20 to 30° C. for 5 hours. At 20 to 40° C., a solution of phosphoric acid (8.5 kg) in water (28.9 L), and water (115.5 L), were sequentially added thereto. At 30 to 40° C., compound A (0.48 kg) was added thereto as seed crystals. The resulting mixture was stirred for 19.5 hours, and then cooled to 20° C. The solid was collected by filtration, and then washed with water (96.3 L). The solid was dried at not more than 50° C., and pulverized to obtain compound A (17.5 kg).

The compound A obtained was identified using IR.

Example 1

Time to Occurrence of Phototoxicity-Related Symptom in Clinical Trial of Compound A for Patients with Erythropoietic Protoporphyria and Patients with X-Linked Porphyria Compound A was administered to adult male and female patients with erythropoietic protoporphyria or X-linked porphyria for 16 weeks in a randomized double-blind clinical trial. As a primary endpoint for the clinical effect, the time to the first symptom due to exposure to light, including indirect sunlight as well as direct sunlight, during the period from 1 hour after sunrise to 1 hour before sunset was evaluated.

The baseline median of the erythrocyte protoporphyrin IX level was determined by measuring the protoporphyrin IX level in the fraction of erythrocytes in blood.

The median of the melanin density was determined h spectrophotometric measurement for the skin at the following six sites: the forehead, the left cheek, the inner side of the right upper arm, the inner side of the left forearm, the right side of the abdomen, and the left side of the hip.

Table 1 shows the evaluation results at week 16 obtained for 35 cases in which placebo was given, 33 cases in which 100 mg of compound A was orally taken once daily, and 34 cases in which 300 mg of compound A was orally taken once daily. The groups in which 100 mg or 300 mg of compound A was administered showed lengths of time of 53.8 minutes and 62.5 minutes, respectively, indicating significant prolongation of the length of time relative to the group in which placebo was administered.

TABLE 1

| Item | Compound A 100 mg (N = 33) vs placebo (N = 35) | Compound A 300 mg (N = 34) vs placebo (N = 35) |
|---|---|---|
| Least squares mean of the length of time (in minutes) before the first occurrence of a symptom in a day | 53.8 | 62.5 |
| P value | 0.008 | 0.003 |

According to analysis of the above item in the patient group whose baseline median of the erythrocyte protoporphyrin IX level was not less than 1980.50 mcg/dL, when 100 mg of compound A was administered, the least squares mean of the time (in minutes) to the first occurrence of the symptom in a day was 69.3 minutes (P value, 0.020), and, when 300 mg of compound A was administered, the least squares mean of the time (in minutes) to the first occurrence of the symptom in a day was 82.6 minutes (P value, 0.003). Thus, both cases showed statistical significance. Also in the patient group whose baseline median of the erythrocyte protoporphyrin IX level was less than 1980.50 mcg/dL, the time to the first occurrence of the symptom in a day tended to be prolonged.

In addition, analysis of the above item was carried out after dividing the subjects into the patient group whose median of the melanin density was not less than 3.0915 and the patient group whose median of the melanin density was less than 3.0915. As a result, in the former group, when 100 mg of the compound was administered, the least squares mean of the time (in minutes) to the first occurrence of the symptom in a day was 85.0 minutes (P value, <0.001), and, when 300 mg of the compound was administered, it was 80.3 minutes (P value, 0.002). In the latter group, when 100 mg of the compound was administered, the least squares mean of the time (in minutes) to the first occurrence of the symptom in a day was 23.2 minutes (P value, 0.499), and, when 300 mg of the compound was administered, it was 63.7 minutes (P value, 0.051), indicating that the effect that prolongs the time to the occurrence of the phototoxicity-related symptom is higher at 300 mg.

Example 2

Time to Occurrence of Phototoxicity-Related Symptom (Clinical Primary Endpoint) in Patients with Erythropoietic Protoporphyria and Patients with X-Linked Porphyria Evaluated for Subgroup in which Initial Dosing of Compound A was Carried Out in Spring or Summer and Subgroup in Which Initial Dosing of Compound A was Carried Out in Fall or Winter The test in Example 2 was conducted in the Northern Hemisphere. Table 2 shows the evaluation results at week 16 obtained for a subgroup in which initial dosing of compound A was carried out in spring or summer (20 cases in which placebo was given, 18 cases in which 100 mg of compound A was orally taken once daily, and 18 cases in which 300 mg of compound A was orally taken once daily) and a subgroup in which initial dosing of compound A was carried out in fall or winter (15 cases in which placebo was given, 15 cases in which 100 mg of compound A was orally taken once daily, and 16 cases in which 300 mg of compound A was orally taken once daily). In the spring-summer subgroup, the groups in which 100 mg or 300 mg of compound A was administered showed lengths of time of 54.4 minutes and 42.2 minutes, respectively, indicating prolongation of the length of time relative to the group in which placebo was administered. In the fall-winter subgroup, the groups in which 100 mg or 300 mg of compound A was administered showed lengths of time of 52.8 minutes and 95.8 minutes, respectively, indicating significant prolongation of the length of time relative to the group in which placebo was administered. Thus, both groups in which 100 mg or 300 mg of compound A was administered showed prolongation of the length of time irrespective of the season.

TABLE 2

| Items | Subgroup in which initial dosing of compound A was carried out in spring or summer | |
|---|---|---|
| | Compound A 100 mg (N = 18) vs Placebo (N = 20) | Compound A 300 mg (N = 18) vs Placebo (N = 20) |
| Least squares mean of the length of time (in minutes) before the first occurrence of a symptom in a day | 54.4 | 42.2 |
| P value | 0.073 | 0.168 |

| Items | Subgroup in which initial dosing of compound A was carried out in fall or winter | |
|---|---|---|
| | Compound A 100 mg (N = 15) vs Placebo (N = 15) | Compound A 300 mg (N = 16) vs Placebo (N = 15) |
| Least squares mean of the length of time (in minutes) before the first occurrence of a symptom in a day | 52.8 | 95.8 |
| P value | 0.029 | <0.001 |

Example 3

Number of Pain Events Recorded in Electronic Diary by Patients During Evaluation Period of 16 Weeks in Clinical Trial of Compound A for Patients with Erythropoietic Protoporphyria and Patients with X-Linked Porphyria.

Compound A was administered to adult male and female patients with erythropoietic protoporphyria or X-linked porphyria for 16 weeks in a randomized double-blind clinical trial. As another endpoint for the clinical effect, the number of pain events during the evaluation period of 16 weeks was recorded in an electronic diary by the patients themselves.

Table 3 shows the evaluation results obtained for 23 cases in which placebo was given, 24 cases in which 100 mg of compound A was orally taken once daily, and 24 cases in which 300 mg of compound A was orally taken once daily. The incidence rates of pain during the evaluation period in the placebo administration group, the 100-mg compound A-administration group, and the 300-mg compound A-administration group were 7.5, 3.3, and 3.5, respectively. Thus, the 100-mg compound A-administration group and the 300-mg compound A-administration group significantly showed reduction of pain events by 60% and 50%, respectively, relative to the placebo administration group (Table 3).

TABLE 3

| Item | Placebo | Compound A 100 mg | Compound A 300 mg |
|---|---|---|---|
| N (number) | 23 | 24 | 24 |
| Incidence rate of pain | 7.5 | 3.3 | 3.5 |
| Ratio to placebo | — | 0.4 | 0.5 |
| P value | — | 0.027 | 0.028 |

Example 4

Evaluation of Health-Related QOL of Patients in Clinical Trial of Compound A for Patients with Erythropoietic Protoporphyria and Patients with X-Linked Porphyria.

Compound A was administered to adult male and female patients with erythropoietic protoporphyria or X-linked porphyria for 16 weeks in a randomized double-blind clinical trial. As a secondary endpoint for the clinical effect, the PGIC (Patient Global Impression of Change) score, which is a health-related QOL, of each patient at week 16 was recorded by the patients themselves, More specifically, each patient was provided with a questionnaire for scoring the degree of improvement of the overall physical and mental health conditions on a 7-point scale. In this case, the score 1 of the PGIC score indicates that no change occurred or that exacerbation occurred, and wherein the score 7 indicates that remarkable improvement was achieved.

Table 4 shows the evaluation results obtained for 30 cases in which placebo was given, 25 cases in which 100 mg of compound A was orally taken once daily, and 24 cases in which 300 mg of compound A was orally taken once daily. The PGIC scores at week 16 in the placebo-administration group, the 100-mg compound A-administration group, and the 300-mg compound A-administration group were 2.9, 6.4, and 6.6, respectively. Thus, the 100-mg compound A-administration group and the 300-mg compound A-administration group showed significant increases in the PGIC score relative to the placebo-administration group, indicating their global impression improvement (Table 4).

TABLE 4

| Item | Placebo | Compound A 100 mg | Compound A 300 mg |
|---|---|---|---|
| N (number) | 30 | 25 | 24 |
| Least squares mean of the scores | 2.9 | 6.4 | 6.6 |
| P value | — | <0.001 | <0.001 |

Example 5

Phase III Trial Using Compound A as Test Substance

Subjects: Male and Female Patients with Erythropoietic Protoporphyria or X-Linked Porphyria, Whose Ages Range from 12 Years Old to 75 Years Old.

Outline of Trial: Randomized Double-Blind Clinical Trial

In 53 cases, placebo is given. In 53 cases. 100 mg of compound A is orally taken once daily. In 53 cases, 200 mg of compound A is orally taken once daily.

Test Items (1) The Time to the Occurrence of a Phototoxicity-Related Symptom in a Clinical Trial of Compound A for Patients with Erythropoietic Protoporphyria and Patients with X-Linked Porphyria In a randomized double-blind clinical trial, compound A is administered to the subjects for 26 weeks, and, depending on conditions, additional administration is carded out for 26 weeks or up to 58 weeks. As a primary endpoint for the clinical effect, the time to the first occurrence of a symptom due to exposure to light in a day is evaluated at week 26.

(2) The Number of Pain Events Recorded in an Electronic Diary by Patients During an Evaluation Period of 26 Weeks in a Clinical Trial of Compound A for Patients with Erythropoietic Protoporphyria and Patients with X-Linked Porphyria In a randomized double-blind clinical trial, compound A is administered to the subjects for 26 weeks, and, depending on conditions, additional administration is carried out for 26 weeks or up to 58 weeks. As another endpoint for the clinical effect, the number of pain events during the evaluation period of 26 weeks is recorded in an electronic diary by the patients themselves.

(3) Evaluation of the Health-Related QOL of Patients in a Clinical Trial of Compound A for Patients with Erythropoietic Protoporphyria and Patients with X-Linked Porphyria In a randomized double-blind clinical trial, compound A is administered to the subjects for 26 weeks, and, depending on conditions, additional administration is carried out for 26 weeks or up to 58 weeks. As a secondary endpoint for the clinical effect, the PGIC (Patient Global Impression of Change) score, which is a health-related QOL, of each patient at week 26 is recorded by the patients themselves. More specifically, each patient is provided with a questionnaire for scoring the degree of improvement of the overall physical and mental health conditions on a 7-point scale. In this case, the lowest score of the PGIC score, 1 point, indicates "Very Much Improved" and wherein the highest score, 7 points, indicates "Very Much Worse".

The invention claimed is:

1. A method for treating porphyria, comprising: administering to a subject in need thereof at least one of 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid, a pharmaceutically acceptable salt thereof, and a pharmaceutically acceptable or cocrystal thereof, wherein a dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid or the pharmaceutically acceptable salt or cocrystal thereof is in a range of 50 to 500 mg/day.

2. The method according to claim 1, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or the pharmaceutically acceptable salt or cocrystal thereof is in a range of 100 to 300 mg/day.

3. The method according to claim 1, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or the pharmaceutically acceptable salt or cocrystal thereof is 100 mg/day, 200 mg/day, or 300 mg/day.

4. The method according to claim 1, wherein the porphyria is erythropoietic protoporphyria, X-linked porphyria, congenital erythropoietic porphyria, variegate porphyria, acute intermittent porphyria, porphyria cutanea tarda, or hereditary coproporphyria.

5. The method according to claim 4, wherein the porphyria is erythropoietic protoporphyria or X-linked porphyria.

6. The method according to claim 1, wherein at least one of the 1-{2-[(3 S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid, the pharmaceutically acceptable salt thereof, and the pharmaceutically acceptable cocrystal thereof is a cocrystal of 1-{2-[(3S,4R)-1-{[(3R, 4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid and phosphoric acid.

7. The method according to claim 1, wherein the porphyria is at least one of erythropoietic protoporphyria, X-linked porphyria, congenital erythropoietic porphyria, variegate porphyria, acute intermittent porphyria, porphyria cutanea tarda, and hereditary coproporphyria.

8. The method according to claim 1, wherein the porphyria is at least one of erythropoietic protoporphyria and X-linked porphyria.

9. The method according to claim 1, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or the pharmaceutically acceptable salt or cocrystal thereof is in a range of 50 to 300 mg/day.

10. The method according to claim 1, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or the pharmaceutically acceptable salt or cocrystal thereof is 50 mg/day, 100 mg/day, 200 mg/day, or 300 mg/day.

11. The method according to claim 1, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or the pharmaceutically acceptable salt or cocrystal thereof is administered intravenously, orally, percutaneously, or topically.

12. The method according to claim 1, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)

phenyl}piperidine-4-carboxylic acid or the pharmaceutically acceptable salt or cocrystal thereof is administered orally.

13. The method according to claim 1, wherein the subject in need thereof is a patient with a history of phototoxic reactions from at least one of erythropoietic protoporphyria and X-linked porphyria.

14. The method according to claim 1, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or the pharmaceutically acceptable salt or cocrystal thereof is administered to the subject in need thereof in the range of 50 to 500 mg/day such that a time to prodromal symptoms including burning, tingling, itching and stinging is increased and that a number of sunlight-induced pain events is decreased.

15. The method according to claim 9, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or the pharmaceutically acceptable salt or cocrystal thereof is administered to the subject in need thereof in the range of 50 to 300 mg/day such that a time to prodromal symptoms including burning, tingling, itching and stinging is increased and that a number of sunlight-induced pain events is decreased.

16. The method according to claim 1, wherein the pharmaceutically acceptable cocrystal of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid is administered to the subject in need thereof in the range of 50 to 500 mg/day.

17. The method according to claim 1, wherein the pharmaceutically acceptable salt of the 1-{2-[(3S,4R)-1-{[(3R, 4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid is administered to the subject in need thereof in the range of 50 to 500 mg/day.

18. The method according to claim 1, wherein the dose of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl) phenyl}piperidine-4-carboxylic acid or the pharmaceutically acceptable salt or cocrystal thereof administered to the subject in need thereof is 50 mg/day, 100 mg/day, 200 mg/day, or 300 mg/day such that a time to prodromal symptoms including burning, tingling, itching and stinging is increased and that a number of sunlight-induced pain events is decreased.

19. The method according to claim 13, wherein the pharmaceutically acceptable cocrystal of the 1-{2-[(3S,4R)-1-{[(3R,4R)-1-cyclopentyl-3-fluoro-4-(4-methoxyphenyl) pyrrolidin-3-yl]carbonyl}-4-(methoxymethyl)pyrrolidin-3-yl]-5-(trifluoromethyl)phenyl}piperidine-4-carboxylic acid is administered orally to the subject in need thereof in the range of 50 to 300 mg/day such that a time to prodromal symptoms including burning, tingling, itching and stinging is increased and that a number of sunlight-induced pain events is decreased.

20. The method according to claim 13, wherein the pharmaceutically acceptable salt of the 1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid is administered orally to the subject in need thereof in the range of 50 to 300 mg/day such that a time to prodromal symptoms including burning, tingling, itching and stinging is increased and that a number of sunlight-induced pain events is decreased.

\* \* \* \* \*

18